(12) United States Patent
Schatz et al.

(10) Patent No.: US 8,150,503 B2
(45) Date of Patent: *Apr. 3, 2012

(54) USE OF PERIODICITY IN MEDICAL DATA ANALYSIS

(75) Inventors: Kelly Schatz, Navarre, FL (US); Robert J. Sweeney, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 151 days.

This patent is subject to a terminal disclaimer.

(21) Appl. No.: 12/502,059

(22) Filed: Jul. 13, 2009

(65) Prior Publication Data

US 2009/0275811 A1 Nov. 5, 2009

Related U.S. Application Data

(63) Continuation of application No. 11/230,298, filed on Sep. 19, 2005, now Pat. No. 7,561,912.

(51) Int. Cl.
*A61N 5/04* (2006.01)
(52) U.S. Cl. ........................ 600/509; 600/513
(58) Field of Classification Search .............. 600/509, 600/513, 515
See application file for complete search history.

(56) References Cited

U.S. PATENT DOCUMENTS

| | | | |
|---|---|---|---|
| 4,510,944 A | 4/1985 | Porges | |
| 6,272,377 B1 | 8/2001 | Sweeney et al. | |
| 6,638,963 B1 | 10/2003 | Lewy et al. | |
| 6,668,196 B1 | 12/2003 | Villegas et al. | |
| 6,694,179 B1 | 2/2004 | Mouchawar et al. | |
| 6,804,656 B1 | 10/2004 | Rosenfeld et al. | |
| 6,811,537 B2 | 11/2004 | Bardy | |
| 7,239,988 B2 | 7/2007 | Hasson et al. | |
| 7,433,827 B2 | 10/2008 | Rosenfeld et al. | |
| 7,454,359 B2 | 11/2008 | Rosenfeld et al. | |
| 7,561,912 B2 | 7/2009 | Schatz et al. | |
| 7,610,324 B2 | 10/2009 | Troyansky et al. | |
| 2004/0204635 A1 | 10/2004 | Scharf et al. | |
| 2007/0067005 A1 | 3/2007 | Schatz et al. | |

OTHER PUBLICATIONS

"U.S. Appl. No. 11/230,298 Non-Final Office Action mailed May 13, 2008", 9 pgs.
"U.S. Appl. No. 11/230,298 Response filed Feb. 10, 2009 to Final Office Action mailed Nov. 10, 2008", 7 pgs.
"U.S. Appl. No. 11/230,298 Response filed Aug. 12, 2008 to Non Final Office Action mailed May 13, 2008", 9 pgs.
"U.S. Appl. No. 11/230,298 Final Office Action mailed Nov. 10, 2008", 10 pgs.
"U.S. Appl. No. 11/230,298 Notice of Allowance mailed Mar. 9, 2009", NOAR, 6 pgs.

*Primary Examiner* — Carl H Layno
*Assistant Examiner* — Brian T Gedeon
(74) *Attorney, Agent, or Firm* — Schwegman, Lundberg & Woessner, P.A.

(57) ABSTRACT

A patient management system is described that includes an implantable device for collecting one or more physiological parameter values and associated timestamps indicating the time at which the value is collected. The system is then configured to determine the periodic variation, if any, of a particular physiological parameter and use that periodicity in assessing changes in the parameter values over time.

20 Claims, 3 Drawing Sheets

USE OF PERIODICITY IN MEDICAL DATA ANALYSIS

CROSS REFERENCE TO RELATED APPLICATION

This application is a continuation of U.S. application Ser. No. 11/230,298, filed Sep. 19, 2005, now issued as U.S. Pat. No. 7,561,912, which is hereby incorporated by reference in its entirety.

FIELD OF THE INVENTION

This invention pertains to methods and apparatus for medical monitoring.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers have been used is in the treatment of bradycardia, where the ventricular rate is too slow. If functioning properly, the pacemaker makes up for the heart's inability to pace itself at an appropriate rhythm in order to meet metabolic demand by enforcing a minimum heart rate and/or artificially restoring AV conduction. Implantable devices may also be configured to treat tachyarrhythmias such as fibrillation with electrical stimulation.

As a part of performing their functions in delivering therapy, implantable cardiac devices may equipped with various sensing modalities for detecting cardiac electrical activity as well as measuring other physiological parameters. Other types of implantable devices may be configured for delivering other types of therapy and/or only monitoring particular physiological parameters. A patient management system may be constructed of an implantable device configured with a telemetry system for communicating such collected data to an external device and ultimately to clinical personnel for evaluation.

SUMMARY

A patient management system is described that includes an implantable device for collecting one or more physiological parameter values and associated timestamps indicating the time at which the value is collected. The system is then configured to determine the periodic variation, if any, of a particular physiological parameter and use that periodicity in assessing changes in the parameter values over time.

DETAILED DESCRIPTION

Figure 1:
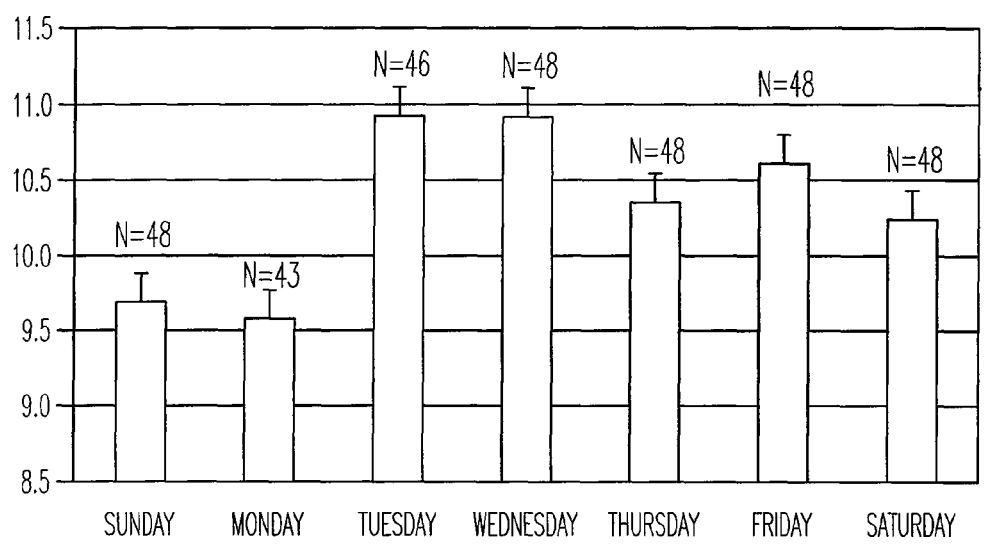
FIG. 1 illustrates collected data from an example patient showing weekly periodicity.

A patient management system that includes an implanted device together with a means for extracting data from the device for communication to a health care professional allows the opportunity to closely monitor the day-to-day health status of a patient. For example, device based diagnostics may be updated daily with measured parameter values stored in a seven day circular buffer and/or weekly with weekly averages of the parameter stored in a 52-week circular buffer. External parameters such as weight and blood pressure can be measured and recorded on a daily, semi-daily, or weekly basis. The communication between an external device and the implanted device allows information from the device to be downloaded and stored by the patient management system. The daily and weekly diagnostic values can be a valuable tool in assessing the health status of the patient on a daily basis and over a course of time. Trends in the device-based diagnostics offer the opportunity to detect gradual or sudden improvement or degradation of the patient's physiologic condition by examining the parameter values over time. The features of a patient management system allow the analysis of the downloaded and stored data to detect changes in the status of the patient, to calculate the probability of an adverse event before it occurs based on the values and trends of the diagnostics, and report these findings to the health care professional in a timely manner.

The ability of a patient management system to monitor patient health status is dependent on the ability of the system to extract information and trends in the daily, semi-daily and/or weekly recorded physiologic parameters. Once the patient management system has downloaded and stored enough data to establish a trend for each diagnostic based on the recorded values over a period of time (which depends on how often the diagnostic is measured), newly acquired values can then be compared to previous values of that parameter. Improvement and deterioration of the status of a patient can then be monitored. Sudden changes in the health status of the patient may lead to changes in the values of certain recorded diagnostics, which can be detected and used to develop a probability of an adverse event occurring in the next x number of days. An algorithm can be incorporated in the patient management system that monitors the recorded diagnostics and calculates the risk of an adverse event each time new physiologic data is downloaded. Therefore, it is important to be as accurate as possible when developing methods of analyzing diagnostics to detect the probability of a deterioration in health condition that made lead to an adverse event, so as not to falsely alert the clinician.

When looking for trends and changes in patient diagnostics that are recorded on a daily or semi-daily basis, it is advantageous to understand and account for any periodicity that may be present in the data. Patients tend to have different routines, environmental factors, and physiological factors (profession, medication doses, menstrual cycle, etc.) that may cause a cyclic variation in the diagnostics on a daily, weekly, monthly, etc. basis. For example, the percent of the day that a patient is active tends to vary significantly over the course of a week such that certain weekdays have significantly lower or higher activity percentages than other days of the week. If a patient has a desk job, their amount of activity on weekdays would likely be much lower than on weekend days, whereas if a patient has a physically demanding job such as a construction worker, their activity would likely be higher during the weekdays and lower on weekends. Similar periodicities can be caused by many factors, and will vary on a per-patient basis.

If one were to analyze this data without accounting for periodicities that exist in each parameter, the magnitude of changes in the diagnostic signal will be less sensitive. In order to accurately detect changes in the patient's health condition, it is advantageous to process the data in a manner that accounts for any periodicities that exist. For example, in the case of the patient who experiences weekly periodicity in the percent of the day active during the course of a week, a low activity two days in a row may have different significance depending on which days of the week they occur. Take the case of a patient who typically has an activity percent of 6% on Tuesdays and Wednesdays and an activity percent of 9% on Saturdays and Sundays. If the device records an activity value of 4% for two consecutive days, it would be much more probable that this is indicative of a decline in the patient's health status were it to occur on a weekend as opposed to a Tuesday and Wednesday. Data values should be processed and analyzed with respect to other like data values. In addition, for the above case, a prediction of what the diagnostic value will be either today or a day in the future will be less accurate if all of the previous daily values are averaged together, or if the days of the week that the values represent are not taken into consideration.

In order to ensure the most accurate interpretation of the device based and external data downloaded and stored in the patient management system, any periodicities that exist should be recognized and accounted for. When the data is stored in the system, there is a timestamp associated with it, recording the date (weekday, month, etc.) and time that the diagnostic was measured. The timestamp can be used to determine the precise conditions (day of week, time of day, etc.), that the data values were recorded. Analysis such as an autocorrelation can be used for each patient diagnostic to detect periodicity in the data signal, and also to determine the time constant of this periodicity. These patterns may differ between patients and parameters. Once any cyclic patterns are detected by a significant difference in the values of a diagnostic with respect to the day (or week, etc.) they are recorded, the patterns are then accounted for during the processing and analysis of that diagnostic parameter.

FIG. 1 is an example of how the average percentage of the day spent active (as recorded by an accelerometer) by a particular patient plotted against the weekday where the daily activity level values are monitored for one year. Error bars represent the standard mean error over each weekday, and the number of daily values in each average is given above each bar. This patient shows a clear periodic trend in the amount of activity according to the day of the week that the value is recorded. In patients who experience such a variation in diagnostics such as their activity level according to the day of the week, comparing daily activity only to other activity values recorded on the same weekday takes into account this weekly periodicity. On a given weekday, say a Monday, instead of averaging all of the daily values over the past x number of weeks and comparing today's recorded value to that average, it would be more appropriate to compare today's value to the average of the past x number of Mondays. This approach would allow a more accurate assessment of the relative change in the diagnostic over time.

This method can be applied to any periodic cycle that a diagnostic parameter may experience. If a patient takes a dose of a certain medication every other day, this is likely to have an effect on certain physiologic diagnostics. Therefore, on days when the patient takes the medication, the recorded value should only be compared to other days on which the patient also took the medication. The recorded timestamp associated with each of the diagnostic values can be used to calculate the conditions (day of the week, time of day, etc.) under which the measurement was made. In the specific case of looking for trends in device-based diagnostics recorded on a daily basis, acknowledging and accounting for the presence of weekly periodicity in parameters such as heart rate variability and activity levels, this approach would yield a more robust and precise detection of changes in patient health status. When creating an algorithm to make predictions on the probability of a future adverse event, it is essential to be as accurate as possible so as to not falsely alert the clinician or be sensitive enough to detect negative changes in the recorded diagnostics. Detecting and processing any periodicities that exist in a stream on diagnostic values will assist in the detection of changes in these physiologic parameters. These changes in diagnostics are important for monitoring the health status of the patient over time, and for predicting future adverse events in a timely and efficient manner.

1. Exemplary Hardware Description

Figure 2:
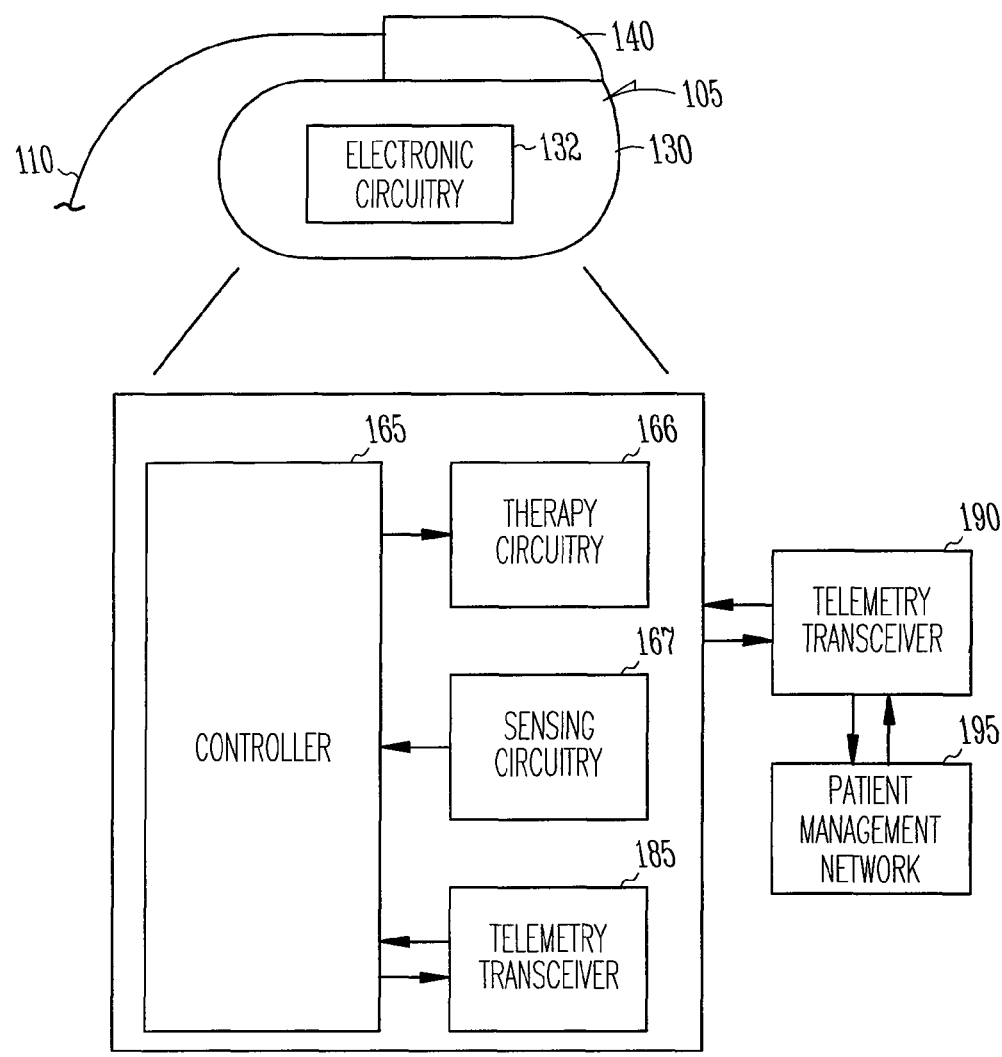
FIG. 2 illustrates an exemplary implantable device.

A system for monitoring physiological parameters as described herein may be implemented in an implantable device configured to perform monitoring only or in a cardiac rhythm management device configured to also deliver cardiac therapies such as bradycardia pacing, cardioversion/defibrillation therapy, or cardiac resynchronization therapy. Implantable cardiac rhythm management devices such as pacemakers and cardioverter/defibrillators are battery-powered devices which are usually implanted subcutaneously on the patient's chest and connected to electrodes by leads threaded through the vessels of the upper venous system into the heart. FIG. 2 illustrates an implantable device 105 that may be, for example, a pacemaker capable of delivering bradycardia and/or antitachycardia pacing, an implantable cardioverter/defibrillator, a combination pacemaker/defibrillator, a drug delivery device, or a monitoring-only device. The device has one or more leads 110 with electrodes for disposition in the right atrium, right ventricle, or in a cardiac vein for sensing cardiac activity and/or delivering electrical stimulation to the heart. One or more of the leads 110 may also be adapted for intra-vascular or other disposition in order to provide other types of sensing functionality. The device 105 includes a hermetically sealed housing 130, formed from a conductive metal, such as titanium, which may serve as an electrode for sensing or electrical stimulation. A header 140, which may be formed of an insulating material, is mounted on housing 130 for receiving the leads 110. Contained within the housing 130 is the electronic circuitry 132 for providing the monitoring functionality to the device as described herein and, in the case of a pacemaker or cardioverter/defibrillator, the circuitry for sensing and stimulating the heart. The electronic circuitry 132 includes a controller 165 which may be made up of discrete circuit elements but is preferably a processing element such as a microprocessor together with associated memory for program and data storage which may be programmed to perform algorithms for monitoring physiological parameters or delivering therapy. Interfaced to the controller 165 are therapy circuitry 166 for delivering electrical stimulation and sensing circuitry 167 for detecting cardiac activity as well as measuring values of other physiological parameters. For example, the sensing circuitry may include an accelerometer, a minute ventilation sensor, a trans-thoracic impedance sensor, an acoustic sensor, and/or a temperature sensor. Also interfaced to the controller 165 is a telemetry transceiver 185 capable of communicating with an external programmer or remote monitoring device 190. An external programmer wirelessly communicates with the device 105 and enables a clinician to receive data and modify the programming of the controller. The remote monitoring device 190 similarly communicates with the device 105 and is further interfaced to a patient management network 195 (e.g., via an internet connection) which allows clinical personnel at remote locations to receive data from the device. As described below, a medical data management device for analyzing physiological parameter data may be incorporated into the programming of the implantable device controller, the remote monitoring device (or an external programmer), or a remotely located server connected to the patient management network.

2. Description of Specific Embodiments

In an exemplary embodiment, a patient management system for analyzing periodic data in the manner described above may be made up of a medical data management device and an implantable medical device such as a pacemaker or defibrillator. The medical data management device is configured to collect values of one or more physiological parameters along with associated timestamps indicative of the times at which the parameter values were measured. The physiological parameter values may be single measurements or may represent values of the parameter averaged over a specified period of time (e.g., daily, weekly, or monthly averages of the parameter value).

The implantable medical device includes one or more sensing modalities for measuring values of one or more physiological parameters and circuitry for collecting and communicating the parameter values to the medical data management device along with associated timestamps indicative of the times at which the parameter values were measured. In one particular embodiment, the medical data management device is an external processing device such as an external programmer or dedicated monitor which communicates with the implantable device via a wireless telemetry link. In another embodiment, the medical data management device is a remotely located computer (e.g., a patient management server) which communicates with an intermediary monitoring device located in the vicinity of the patient over a network (e.g., an internet or phone connection). The implantable medical device communicates measured parameter values to the monitoring device via a wireless telemetry link, and the intermediary monitoring device relays the parameter values measured by the implantable medical device to the medical data management device over the network. In still another embodiment, the medical data management device is not a separate device but is implemented as code executed by the controller of the implantable medical device.

Examples of physiological parameters which may be measured by the implantable device and communicated to the medical data management device include heart rate, an estimate of heart rate variability, activity level (e.g. as measured by an accelerometer), minute ventilation, estimate of cardiac output (e.g., as measured by a trans-thoracic impedance sensor), respiratory rate, amplitudes or other characteristics of heart sounds, and the presence of pulmonary congestion. Physiological parameter values acquired by means other than the implantable device may also be collected and communicated to the medical data management device. Examples of such externally communicated physiological parameters could include blood pressure, body weight, patient responses to health questions, blood glucose levels, and the occurrence of a medication dose. Externally communicated physiological parameter values may be manually input to the medical data management device or an intermediary device or may be performed by a means integral to the medical data management device or an intermediary device. In an example embodiment, externally communicated physiological parameter values are input to an intermediary monitoring device which then relays those values and the parameter values communicated to it by the implantable device (along with their associated timestamps) to the medical data management device over a network connection.

For each physiological parameter, whether externally communicated or acquired by the implantable device, the collected parameter values and timestamps constitute a time series which can be analyzed for periodicity. The medical data management device is further configured to determine the periodic variation, if any, of a particular physiological parameter using the parameter values and associated timestamps. For example, the periodic variation of a physiological parameter may be determined by computing an autocorrelation function ACF of the time series of collected parameter values $X_i$:

$$ACF = E[(X_i - \mu)(X_{i+k} - \mu)]$$

where E denotes the expected value function, i is time index which assumes equal time intervals between consecutive values, $\mu$ is the mean value of the parameter, and k is the time shift or lag value for which the autocorrelation function is being computed. The period or periods at which the parameter varies may then be identified as the lag value(s) at which the autocorrelation function exhibits a peak(s).

The medical data management device may be further configured to compare a present value of a parameter with a previous value of the parameter in a manner which takes into account the periodic variation of the parameter. For example, the medical data management device may compare a present value of a parameter with a previous value of the parameter measured at a time such that the time interval between the measurement times of the present and previous parameter values is equal to a period of the periodic variation of the parameter. In particular examples, the medical data management device compares a present value of a parameter with a previous value of the parameter, wherein the present and previous values of the parameter are measured at a similar time of day, day of the week, or day of the month in accordance with whether the periodic variation of the parameter is daily, weekly, or monthly, respectively. The present value of the parameter may represent the values of the parameter averaged over a first period of time, and the previous value of the parameter may represent the values of the parameter averaged over a second period of time, the previous value of the parameter being regarded as a baseline value. For example, the present value could be the average of the parameter on a Wednesday, and the previous value could be the average value of the parameter over the previous ten Wednesdays. The medical data management device may then be configured to set an alarm if the difference between the present and previous values of one or more parameters exceeds a specified threshold or exceeds a specified threshold for a specified number of times or over a specified period of time. Such an alarm can be used to alert clinical personnel that some sort of intervention may be warranted. The specified thresholds may be made to vary according to the point within a period that the parameter is measured. For example, in the case of a weekly period, different thresholds may used to different days of the week. Using different thresholds for detecting a significant variation from baseline of a parameter can be used to take into account different random variability of the parameter on different days of the week.

In other embodiments, the medical data management device is further configured to identify physiological parameters having similar periodic variations, which information may be useful to clinical personnel in diagnosis or in making treatment decisions. Also, because the periodicity of a particular physiological parameter may change over time, the medical data management device may be further configured to use the collected values of a physiological parameter to periodically re-determine the periodic variation of that parameter and may also set an alarm if the periodic variation of a particular physiological parameter changes by a specified threshold amount.

Figure 3:
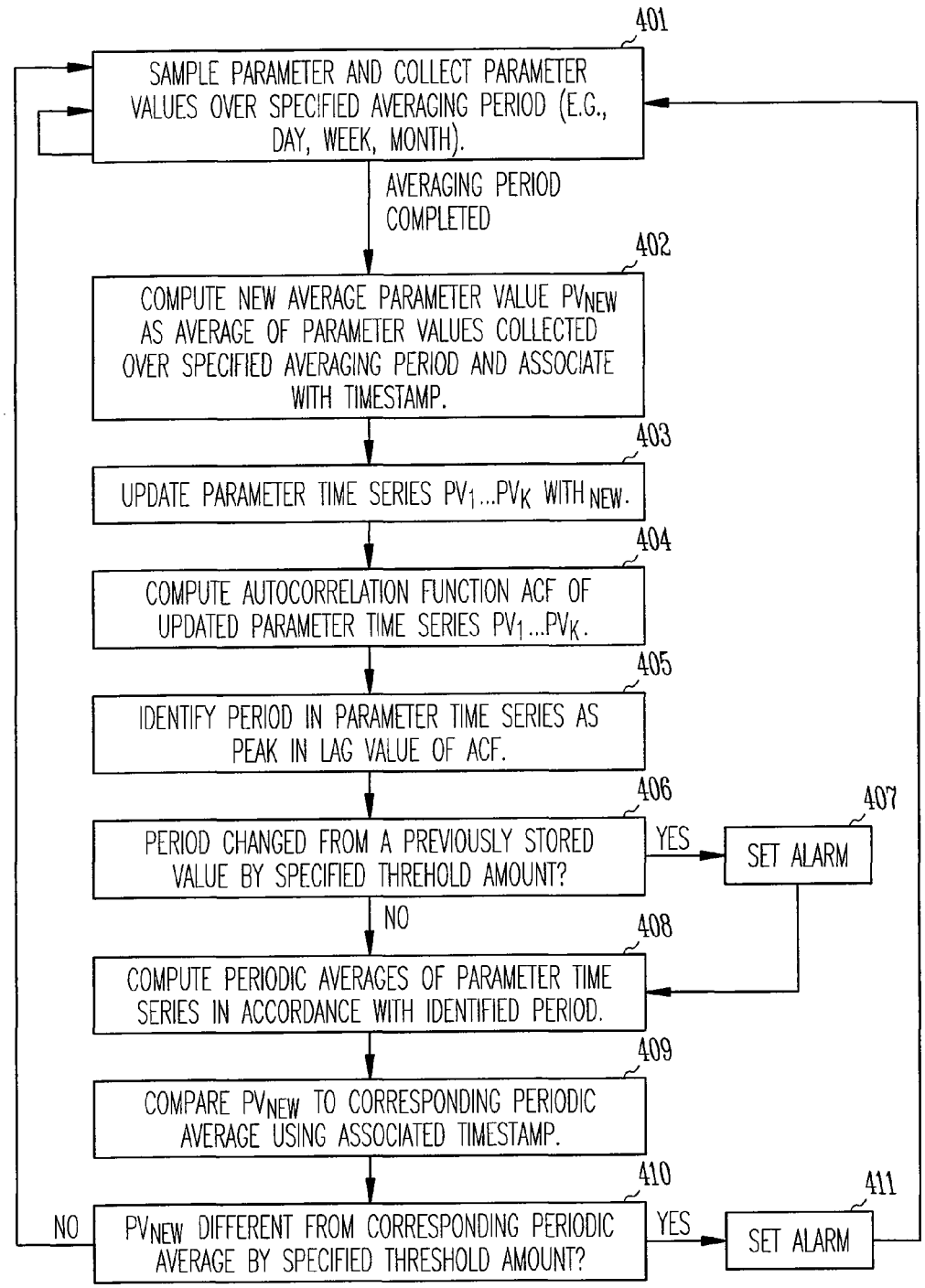
FIG. 3 illustrates an exemplary algorithm.

FIG. 3 illustrates one possible way in which a scheme for assessing periodic parameter data as described above could be implemented as an algorithm executed by the medical data management device. At step 401, a physiological parameter is periodically sampled or computed, and the parameter values are collected over a specified averaging period. The averaging period would normally be selected so that normal random variation in the parameter is averaged out and could be, for example, an hour, a day, a week, or a month. At step 402, the collected parameter values are averaged over the specified averaging period and associated with a timestamp indicative of the time at which the parameter values were collected (e.g., the particular day, week, or month). The averaged parameter value is designated as $PV_{new}$. A time series of such averaged parameter values, $PV_1 \ldots PV_k$, is maintained in an order corresponding to their timestamps. For example, in the case of a daily averaging period, the time series would be the average daily value of the parameter for each of the last k days, k being a specified integer. At step 403, the parameter time series $PV_1 \ldots PV_k$ is updated with $PV_{new}$ by, for example, appending $PV_{new}$ to the end of series and discarding the oldest value $PV_1$. At step 404, the autocorrelation function ACF of the updated parameter time series $PV_1 \ldots PV_k$ is computed. The dominant periodicity in the series is reflected as the lag value at which the autocorrelation function exhibits a maximum. A single peak at a zero lag value, for example, would indicate no periodicity (or a period of 0) in the series, while a maximum at a lag value of n would indicate that the time series has a period of n. (A parameter time series could also exhibit multiple or secondary maxima, and such additional periodicity can be treated similarly.) The lag value at which the maximum occurs is identified as a period of the time series at step 405. At step 406, the presently identified period is compared with a previously found period for the series, and if the period has changed by specified threshold amount, an alarm is set at step 407 to alert clinical personnel that the periodicity of the particular physiological parameter has changed. The previously found period with which the presently identified period is compared may be a long-term average that is periodically updated. At step 408, periodic averages of the parameter time series are computed in accordance with the identified period. For example, a time series of daily average values could have a periodicity of 7, indicating that the value of the parameter tends to repeat every week. The periodic averages of the time series would then consist of average parameter values for each day of the week. At step 409, the new parameter value $PV_{new}$ is compared with the corresponding periodic average using the associated timestamp. For example, in the case of a time series with weekly periodicity, $PV_{new}$ would be compared with the average daily parameter value for the same day of week on which it was collected. If the difference between $PV_{new}$ and the periodic average exceeds a specified threshold (or exceeds the threshold for a specified number of times), as determined at step 410, an alarm is set at step 411.

In another particular embodiment, the medical data management device is further configured to compute a health status parameter as a function of the differences between the present and past values of one or more physiological parameters. Such a health status parameter may be, for example, a weighted average of the deviations of various physiological parameter values from their baseline values that thus represents a kind of composite parameter that clinical personnel may use to determine if the patient's condition is improving or worsening. The medical data management device may also compute trends in the values of a physiological parameter that takes into account the periodicity of the parameter. For example, trends may be computed for parameter values that are measured at a similar time of day, day of the week, or day of the month in accordance with whether the periodic variation of the parameter is daily, weekly, or monthly, respectively.

In another embodiment, the medical data management device may be configured to compute the conditional probability of an adverse health event as a function of the differences between the present and past values of one or more physiological parameters, taking into account the periodic variation of the parameter, or changes in the periodicity of one or more parameters. Such adverse health events may be, for example, cardiac arrhythmias or decompensation events. Computation of conditional probabilities may be performed using techniques described in U.S. Pat. No. 6,272,377, assigned to Cardiac Pacemakers, Inc. and hereby incorporated by reference, where a change in the value of one or more physiological parameters from its baseline value by a specified threshold amount, or a change in the periodicity of a parameter by a specified threshold amount, is regarded as a conditioning event. An adverse event may then be predicted by: 1) detecting a conditioning event statistically associated with the particular adverse event; 2) computing a conditional adverse event probability for the conditioning event from past observations of instances in which the conditioning event occurs alone or together with the adverse event within a specified time period; 3) computing an estimated adverse event probability based upon the detected occurrence of the conditioning event; and 4) predicting the occurrence of the adverse event within a specified prediction time period if the estimated adverse event probability exceeds a specified threshold value.

In one embodiment, the conditional adverse event probability is calculated as a ratio of the number of observed instances in which the conditioning event is followed by the adverse event within a specified basic time period, to the total number of observed instances of the conditioning event. In that case, the estimated probability for the adverse event to occur within the specified basic time period after detection of the conditioning event is simply the calculated conditional adverse event probability. In another embodiment, the conditional adverse event probability CP is calculated by the expression:

$$CP = 1 - e^{-RT}$$

which assumes a Poisson probability distribution, where T is a measure of the specified prediction time period, and R is an estimate of the rate at which the particular adverse events occur while the conditioning event is present. The rate R is a ratio of: 1) the number of instances in which the conditioning event is followed by the adverse event within a specified basic time period, to 2) the length of the basic time period multiplied by the total number of basic time periods in which the conditioning event is observed. The estimated probability for the adverse event to occur within the time T after detection of the conditioning event is again the conditional adverse event probability. Calculating the conditional probability in this manner allows the prediction time period T to differ from the length of the basic time period used to derive the conditional adverse event probability.

The past observations of the occurrences of conditioning events and adverse events from which the conditional adverse event probabilities are derived can be taken from either population data or from data collected in real-time from a particular patient. In one embodiment, the conditional adverse event probabilities are based initially upon past observations of the occurrences of conditioning events and adverse events taken from population data, and each probability is subsequently updated in accordance with observations taken in real-time from a particular patient. For example, a conditional adverse event probability may be updated only if its new value differs by a predetermined amount from its old value. In another embodiment, the amount by which the new value differs from the old value is tested for statistical significance before a conditional adverse event probability is updated. In another embodiment, the old value of the conditional adverse event probability is incremented or decremented by a specific amount after a prediction time period following a conditioning event in accordance with whether the adverse event occurred or not, respectively. In another embodiment, the statistical association between the conditioning event and the occurrence of the adverse event is periodically reevaluated using the most recent patient-specific data. If the statistical association (e.g., as a calculated from a chi-square test) is found to be below a specified value, the use of that conditional adverse event probability is discontinued.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A method comprising:
configuring a medical data management device to collect values of one or more physiological parameters along with associated timestamps indicative of the times at which the parameter values were measured;
configuring an implantable medical device that includes circuitry for measuring values of one or more physiological parameters to communicate the parameter values to the medical data management device along with associated timestamps indicative of the times at which the parameter values were measured; and,
configuring the medical data management device to use the timestamps associated with the collected parameter values of a physiological parameter to measure the periodic variation, if any, of that particular physiological parameter, and wherein the periodic variation of a physiological parameter is determined by computing an autocorrelation function of a time series of collected parameter values.

2. The method of claim 1 wherein the physiological parameter values and associated timestamps collected by the medical data management device include one or more parameter values and timestamps as communicated to the medical management device via wireless telemetry.

3. The method of claim 1 further comprising configuring the medical data management device to identify the period or periods at which the parameter varies as the lag value at which the autocorrelation function exhibits a peak.

4. The method of claim 1 wherein the physiological parameter values represent values of the parameter averaged over a specified period of time.

5. The method of claim 1 further comprising configuring the medical data management device to compare a present value of a parameter with a previous value of the parameter in a manner which takes into account the periodic variation of the parameter.

6. The method of claim 5 wherein the present value of the parameter represents the values of the parameter averaged over a first period of time and wherein the previous value of the parameter represents the values of the parameter averaged over a second period of time, the previous value of the parameter being regarded as a baseline value.

7. The method of claim 6 further comprising configuring the medical data management device to set an alarm if the difference between the present and previous values of one or more parameters exceeds a specified threshold a specified number of times or over a specified period of time.

8. The method of claim 5 further comprising configuring the medical data management device to compute a health status parameter as a function of the differences between the present and past values of one or more physiological parameters.

9. The method of claim 5 further comprising configuring the medical data management device to compute the conditional probability of an adverse health event as a function of the differences between the present and past values of one or more physiological parameters.

10. The method of claim 1 further comprising configuring the medical data management device to compare a present value of a parameter with a previous value of the parameter measured at a time such that the time interval between the measurement times of the present and previous parameter values is equal to a period of the periodic variation of the parameter.

11. The method of claim 10 further comprising configuring the medical data management device to compare a present value of a parameter with a previous value of the parameter, wherein the present and previous values of the parameter are measured at a similar time of day, day of the week, or day of the month in accordance with whether the periodic variation of the parameter is daily, weekly, or monthly, respectively.

12. The method of claim 1 further comprising configuring the medical data management device to identify parameters with similar periodic variations.

13. The method of claim 1 further comprising configuring the medical data management device to use the collected values of a physiological parameter to periodically re-determine the periodic variation of that parameter.

14. The method of claim 1 further comprising configuring the medical data management device to set an alarm if the periodic variation of a particular physiological parameter changes by a specified threshold amount.

15. The method of claim 1 further comprising configuring the medical data management device to compute a trend in the values of a physiological parameter that are measured at a similar time of day, day of the week, or day of the month in accordance with whether the periodic variation of the parameter is daily, weekly, or monthly, respectively.

16. The method of claim 1 wherein the one or more physiological parameters measured by the implantable medical device includes heart rate.

17. The method of claim 1 wherein the one or more physiological parameters measured by the implantable medical device includes an estimate of heart rate variability.

18. The method of claim 1 wherein the one or more physiological parameters measured by the implantable medical device includes a measurement of exertion level.

19. The method of claim 1 further comprising configuring the medical data management device to use timestamps associated with collected parameter values of an externally communicated physiological parameter not measured by the implantable device to measure the periodic variation, if any, of the externally communicated physiological parameter, and wherein the periodic variation is determined by computing an autocorrelation function of a time series of collected parameter values.

20. A patient management system, comprising:
a medical data management device configured to collect values of one or more physiological parameters along with associated timestamps indicative of the times at which the parameter values were measured;
an implantable medical device that includes circuitry for measuring values of one or more physiological parameters and circuitry for communicating the parameter values to the medical data management device along with associated timestamps indicative of the times at which the parameter values were measured; and,
wherein the medical data management device is further configured to use the timestamps associated with the collected parameter values of a physiological parameter to measure the periodic variation of that particular physiological parameter based upon a time series of collected parameter values.

* * * * *